(12) United States Patent
Vitto et al.

(10) Patent No.: US 11,383,066 B2
(45) Date of Patent: Jul. 12, 2022

(54) GUIDEWIRE SYSTEMS AND METHODS FOR PREVENTING WIRE ADVANCEMENT INTO THE BODY DURING CATHETERIZATION

(71) Applicant: Virginia Commonwealth University, Richmond, VA (US)

(72) Inventors: Michael Vitto, Richmond, VA (US); Nicholas Brown, Richmond, VA (US); Chandana Muktipaty, Richmond, VA (US); Kashyap Venuthurupalli, Richmond, VA (US); Teri-Yae Yarbrough, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 128 days.

(21) Appl. No.: 16/838,204

(22) Filed: Apr. 2, 2020

(65) Prior Publication Data

US 2021/0016059 A1    Jan. 21, 2021

Related U.S. Application Data

(60) Provisional application No. 62/801,516, filed on Feb. 5, 2019.

(51) Int. Cl.
*A61M 25/01* (2006.01)
*A61M 25/09* (2006.01)
(Continued)

(52) U.S. Cl.
CPC .... *A61M 25/0113* (2013.01); *A61M 25/0053* (2013.01); *A61M 25/0606* (2013.01);
(Continued)

(58) Field of Classification Search
CPC .......... A61M 2025/09125; A61M 2025/0681; A61M 2025/0293; A61M 2025/09108; A61M 2025/09116; A61M 2025/09133; A61M 2025/09141; A61M 2025/0915; A61M 2025/09158; A61M 2025/09175; A61M 2025/09183; A61M 2025/09191; A61M 2025/09008; A61M 2025/0006;
(Continued)

(56) References Cited

U.S. PATENT DOCUMENTS 5,344,439 A * 9/1994 Otten .................... A61M 25/02
604/105
5,497,782 A    3/1996 Fugoso
(Continued)

FOREIGN PATENT DOCUMENTS

CN    104759022 A *  7/2015  ........ A61M 25/0147
DE    102015003026 B3 *  5/2016  ........ A61M 25/0618
(Continued)

*Primary Examiner* — Nathan R Price
*Assistant Examiner* — Adam J. Cermak
(74) *Attorney, Agent, or Firm* — WCF IP

(57) ABSTRACT

A guidewire and catheter are disclosed which are configured together so that it is not possible to advance the guidewire into the patient where it may be undesirably retained in the patient. The improved safety is achieved by protrusions on each of the guidewire and catheter which coordinate with one another. Novel methods of catheterization are also disclosed.

9 Claims, 14 Drawing Sheets

(51) Int. Cl.
  *A61M 25/06* (2006.01)
  *A61M 25/00* (2006.01)
(52) U.S. Cl.
  CPC ........ *A61M 25/0662* (2013.01); *A61M 25/09* (2013.01); *A61M 2025/0687* (2013.01); *A61M 2025/09125* (2013.01)
(58) Field of Classification Search
  CPC .......... A61M 25/0169; A61M 25/0662; A61M 25/0029; A61M 25/09025; A61M 25/09016; A61M 25/09; A61M 25/09033; A61M 25/09041; A61M 25/0905; A61M 25/0105; A61M 25/0172
  USPC .................................................. 604/104–107
  See application file for complete search history.

(56) References Cited

U.S. PATENT DOCUMENTS

| | | | | |
|---|---|---|---|---|
| 6,616,680 B1 * | 9/2003 | Thielen | ............. | A61F 2/013 606/200 |
| 6,743,247 B1 * | 6/2004 | Levinson | ............. | A61F 2/013 606/200 |
| 6,887,256 B2 * | 5/2005 | Gilson | ............. | A61F 2/013 606/200 |
| 6,974,469 B2 * | 12/2005 | Broome | ............. | A61F 2/013 606/200 |
| 7,172,614 B2 * | 2/2007 | Boyle | ............. | A61F 2/013 606/200 |
| 7,331,973 B2 * | 2/2008 | Gesswein | ............. | A61F 2/011 606/200 |
| 7,479,151 B2 | 1/2009 | Rosenschein et al. | | |
| 7,736,385 B2 * | 6/2010 | Agnew | ............. | A61F 2/90 623/1.12 |
| 7,892,251 B1 * | 2/2011 | Kellerman | ............. | A61M 25/09 606/200 |
| 8,034,074 B2 * | 10/2011 | Garner | ............. | 606/200 |
| 8,211,087 B2 | 4/2012 | Carter et al. | | |
| 8,292,872 B2 * | 10/2012 | Soetermans | ............. | A61M 25/09041 604/523 |
| 9,138,307 B2 * | 9/2015 | Valaie | ............. | A61B 17/320725 |
| 9,144,510 B2 * | 9/2015 | Havel | ............. | A61F 2/95 |
| 9,364,209 B2 * | 6/2016 | Voss | ............. | A61B 17/0057 |
| 9,681,888 B2 * | 6/2017 | Schaeffer | ............. | A61B 17/3207 |
| 9,775,782 B2 * | 10/2017 | Delegge | ............. | A61J 15/0061 |
| 9,867,729 B2 * | 1/2018 | Ducke | ............. | A61F 2/966 |
| 10,668,258 B1 * | 6/2020 | Calhoun | ............. | A61M 25/0054 |
| 2003/0097138 A1 * | 5/2003 | Reydel | ............. | A61M 25/0043 606/108 |
| 2004/0158280 A1 * | 8/2004 | Morris | ............. | A61M 25/0136 606/200 |
| 2005/0131343 A1 * | 6/2005 | Abrams | ............. | A61M 25/0662 604/95.04 |
| 2006/0041303 A1 | 2/2006 | Israel | | |
| 2007/0255217 A1 * | 11/2007 | Burkett | ............. | B29C 48/05 604/164.13 |
| 2008/0262430 A1 * | 10/2008 | Anderson | ............. | A61B 17/3415 604/164.1 |
| 2010/0268029 A1 * | 10/2010 | Phan | ............. | A61M 25/09 600/115 |
| 2011/0218529 A1 * | 9/2011 | Garcia | ............. | A61M 25/04 606/41 |
| 2012/0289996 A1 * | 11/2012 | Lee | ............. | A61F 2/012 606/200 |
| 2013/0282036 A1 * | 10/2013 | Schaeffer | ............. | A61B 17/3207 606/159 |
| 2015/0133892 A1 * | 5/2015 | Joe | ............. | A61M 25/09 604/509 |
| 2016/0045715 A1 | 2/2016 | Galgano et al. | | |
| 2018/0304049 A1 | 10/2018 | Bennett et al. | | |
| 2019/0240461 A1 | 8/2019 | Dayton et al. | | |
| 2019/0262587 A1 * | 8/2019 | Gottlieb | ............. | A61M 25/09041 |
| 2020/0230353 A1 * | 7/2020 | Burkholz | ............. | A61M 25/0026 |
| 2020/0360669 A1 * | 11/2020 | Dacanay | ............. | A61M 25/09041 |

FOREIGN PATENT DOCUMENTS

| | | | | |
|---|---|---|---|---|
| ES | 2716238 T3 * | 6/2019 | ........ | A61B 17/2202 |
| WO | WO-0240090 A1 * | 5/2002 | ............. | A61F 2/013 |
| WO | WO-2008138352 A1 * | 11/2008 | ........ | A61M 25/0017 |

* cited by examiner

GUIDEWIRE SYSTEMS AND METHODS FOR PREVENTING WIRE ADVANCEMENT INTO THE BODY DURING CATHETERIZATION

CROSS-REFERENCE TO RELATED APPLICATIONS

This application claims the benefit of U.S. Provisional Application No. 62/801,516, filed Feb. 5, 2019, the complete contents of which are herein incorporated by reference.

FIELD OF THE INVENTION

The invention generally relates to the use of guidewires during catheterization and, in particular, reducing or preventing unintentional advancement of guidewires during procedures such a central venous catheterization.

BACKGROUND

Guidewires have extensive use in vascular access and are routinely used in intravenous catheter placements in veins and arteries. Many medical specialties utilize them on a daily basis including emergency medicine, critical care, surgery, interventional radiology, vascular surgery, cardiology, and pediatrics. In addition, guidewires are used for stent placement, feeding tube placement, and drainage tube placement in many medical specialties.

Center venous catheters (CVCs) are often used in circumstances such as simultaneous delivery of multiple drugs to a patient, long term therapies, frequent blood tests, chemotherapy treatments, and even self-treatment for some patients. Center venous catheter (CVC) misplacement and improper removal create significant patient safety risks. Specifically, CVC guidewire placement is a highly variable step in placement of these catheters. Over five million central venous catheters are placed each year in the United States. Iatrogenic central line problems compromise patient safety and increase hospital costs. Roughly 1 in every 3,000 central line placements result in complications due to loss of the guidewire. Of these, approximately 20% result in patient death.

Efforts exist within some healthcare systems for CVC placement standardization and safety. There has been literature surrounding education, resources, and checklists in attempts to reduce the risk of guidewire misplacement and central line associated infections. These initiatives are met with variable success. Typical guidelines or checklists for standardization of CVC placement demand increased staffing, time for implementation, and frequent retraining for new staff. In addition, given the ubiquitous use of CVC throughout the health system, implementation of a coordinated, consistent, and uniform approach entails many resources, hours of training, and buy-in from many stakeholders and departments.

A safer central line wire would reduce the need for invasive interventional radiology or vascular surgery interventions. A central line guidewire that could not be misplaced in the patient would reduce unnecessary procedures, reduce hospital length of stays, improve confidence in providers and hospital systems, and decrease risk of litigation. Hospitals will realize value, including decreased length of stay, reduction of high-risk procedures, reduction of potential litigation, and increased patient satisfaction.

SUMMARY

According to some embodiments, a new, improved guidewire is disclosed which is unable to be unintentionally advanced and retained in the patient. In spite of potential differences in catherization procedures from one medical professional to the next, the guidewire device itself mechanically reduces or prevents unintentional advancement. As a result, catherization procedures are simpler, safer, and more universal with respect to this issue. Generally, existing procedures for catherization do not require any changes when incorporating improved guidewires according to present embodiments. Exemplary guidewires according to this disclosure have global applications given the use of CVC throughout healthcare worldwide.

A new guidewire has one or more protrusions, such as ridges, and a new catheter has one or more cooperating protrusions. Once the protrusion on the catheter passes the protrusion on the guidewire, the guidewire is retained by the catheter and can no longer get lost in the patient.

According to further embodiments, new methods of catheterization are disclosed in which the risk of unintentional advancement and potential loss of the guidewire in a patient are reduced, but the total number of steps to catheterization are not increased. In one exemplary method, the order of dilation and guidewire placement is uniquely varied from existing methods with a result of actually reducing the number of steps in existing procedures.

DETAILED DESCRIPTION

Figure 1A:
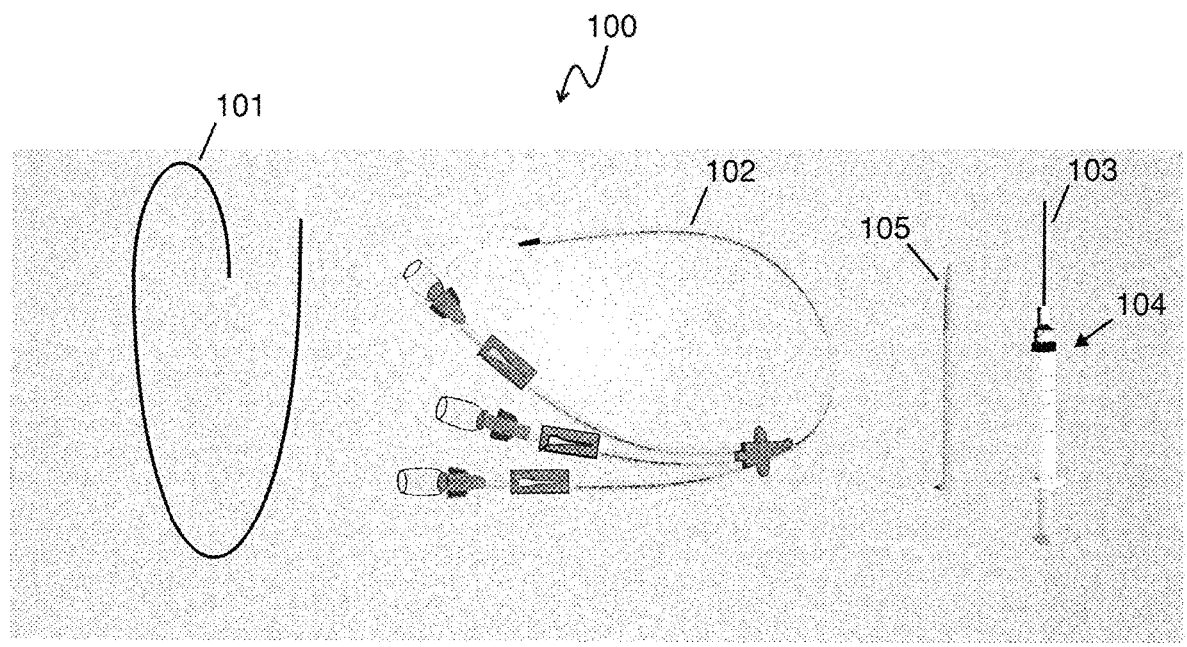
FIG. 1A is a system of tools collectively used to perform catheterization.

FIG. 1A shows an exemplary system 100 comprising (or consisting of) tools usable to perform catheterization. Generally, the system 100 includes a guidewire 101, catheter 102, and a syringe 104. The system 100 may also include a dilator 105 and extensions and attachments for the catheter. The syringe 104 includes a needle 103, a barrel, and a plunger. Note that "guide wire" and "guidewire" are equivalent terms as used herein. For uniformity, the use of "guidewire" will be favored.

Figure 1B:
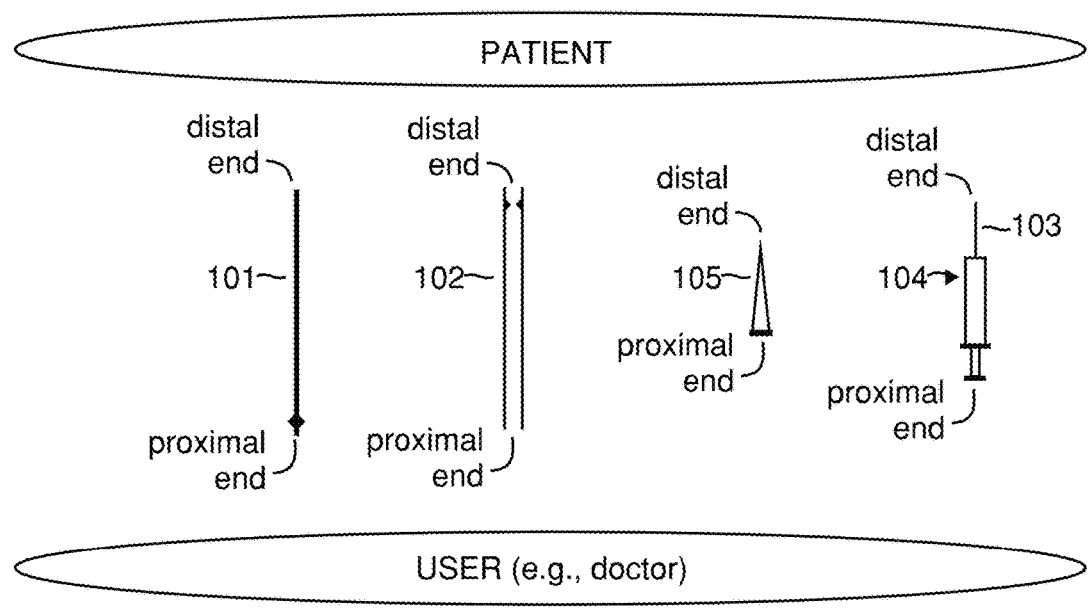
FIG. 1B shows a schematic of catheterization tools with orientation labels.

FIG. 1B is a schematic of the tools of system 100 showing the orientation-labeling convention used in this disclosure. For each device 101, 102, 105, 104, and 103, as well as any other devices or components thereof, a "distal end" and a "proximal end" of such device or component are distinguishable from one another based on their orientations with respect the patient and the user (e.g., medical practitioner, doctor, nurse, technician, etc.). The end of the device or component nearest the patient is the "distal" end. The end of the device or component nearest the doctor is the "proximal" end. Furthermore, in this disclosure "proximal" and "distal" may be used in this manner to qualify nouns other than "end." For instance, the "distal half" of a needle is the half nearest to the patient and furthest from the user, whereas a "proximal half" of a needle is the half nearest to user and furthest from the patient. "End" as used herein may be used to refer to one or more of the endpoint, endplane, or some end portion or part of a thing, e.g. that portion or part which occupies the most-distal or most-proximal 10%, 20%, or 30% volume of the object, or most-distal or most-proximal part constituting the last 10%, 20%, or 30% of the total (longitudinal) length of the object.

Figure 2A:
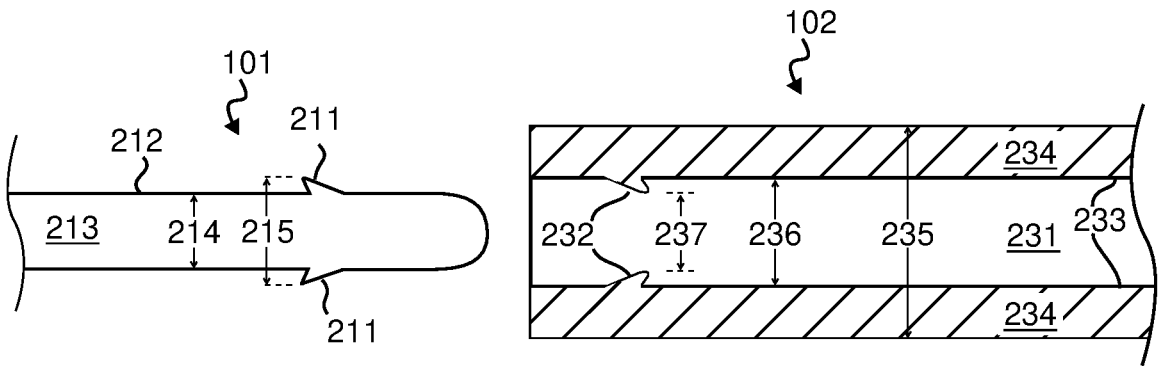
FIG. 2A shows a proximal end of a guidewire and a distal end of a catheter according to an exemplary embodiment in which the guidewire and catheter have respective protrusions configured to cooperate with one another to reduce or prevent occurrence of unintentional guidewire advancement and potential loss in a patient.

FIG. 2A shows a proximal end of a guidewire 101 and a distal end of a catheter 102. For ease of feature illustration, FIG. 2A shows feature profiles within a two-dimensional plane taken along a longitudinal center line of the guidewire 101 and catheter 102. Together the guidewire 101 and catheter 102 are configured to cooperate with one another to reduce or prevent unintentional advancement of the guidewire into a patient during a catheterization procedure such as center venous catheter (CVC) placement.

The guidewire 101 has at least one guidewire protrusion 211 on an external surface 212 of the guidewire 101. The protrusion 211 protrudes from a main body 213. The catheter 102 as a lumen 231 and at least one catheter protrusion 232 on an internal surface 233 of the catheter 102. The protrusion 232 protrudes from the inner surface 233 of the wall 234 of the catheter 102 into the lumen 231.

A "protrusion" may be a ridge, a tooth, a flange, an annulus, a catch, a stop, a tine, or some combination of these. A protrusion may wrap/extend about an entire circumference of a lumen or a guidewire. Alternatively, a protrusion may wrap/extend about less than an entire circumference of a lumen or a guidewire.

Depending on the embodiment, the proximal end of the guidewire 101 may have radial symmetry, bilateral symmetry, and/or rotational symmetry. Depending on the embodiment, the distal end of the catheter 102 may have radial symmetry, bilateral symmetry, and/or rotational symmetry. In most cases the guidewire 101 (in particular the body 213 thereof) is substantially cylindrical and elongate, with a length of, for example, 50 to 100 cm, more often 40 to 80 cm, e.g. 60 cm. The guidewire 101 has a main body 213 with a diameter 214. The guidewire has an increased diameter 215 at the longitudinal position where the protrusion 211 is located. The diameter 215 is greater than the diameter 214.

The catheter 102 is also generally cylindrical and elongate with a wall 234 that defines a diameter 235. The catheter 102 has a lumen 231 with a diameter 236. The thickness of the wall 234 is half of the difference between diameters 235 and 236. The catheter 102 has a reduced diameter 237 at the longitudinal position where the protrusion 232 is located. The catheter's total length may be any length typically used in catheterization procedures.

The diameter 214 of the guidewire 101 is smaller than the diameter 236 of the lumen 231 of the catheter 102. The diameter 214 of the guidewire 101 is less than or equal to the diameter 237 of the catheter 102 at the location of the catheter's protrusion 232. As a result, the main body 213 of the guidewire 101 can generally move freely inside the lumen 231 of the catheter 102. By contrast the diameter 215 of the guidewire 101 at the location of protrusion 211 is larger than the diameter 237 of the catheter 102 at the location of protrusion 232. The sizes, shapes, and arrangement of the protrusions 211 and 232 are configured to cooperate and selectively interact with one another such that (i) the catheter protrusion 232 is moveable past the guidewire protrusion 211 in a first direction and (ii) the catheter protrusion 232 is immovable past the guidewire protrusion 211 in a second direction. The first and second directions are opposite one another. Generally, the first direction involves movement of the catheter toward a patient, and the second direction involves movement of the catheter away from the patient. In FIG. 2A, the first direction is page left, and the second direction is page right.

Figure 2B:
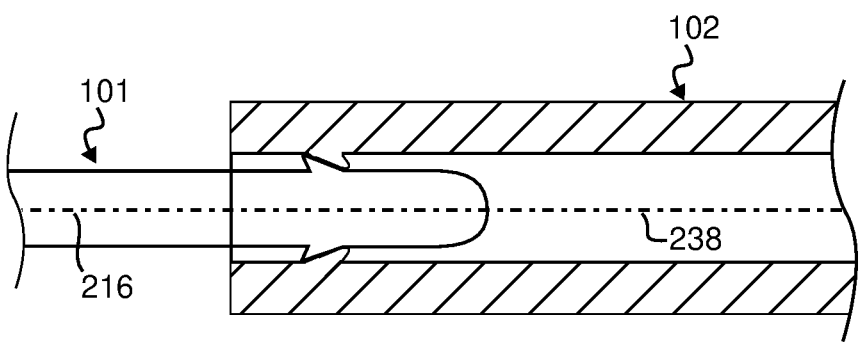
FIG. 2B shows the protrusions of the guidewire and catheter meeting at the same longitudinal location as the catheter is moved over the guidewire.

FIG. 2B shows the guidewire 101 and the catheter 102 of FIG. 2A after the distal end of the catheter 102 has been advanced over the proximal end of the guidewire 101 and the respective protrusions 211 and 232 are in full contact with one another. Further movement of the catheter 102 over the guidewire 101 results in the protrusions exerting forces upon one another. This may result in temporary deflection of the protrusion 232 and/or temporary elastic expansion of the diameters 235, 236, and 237. The catheter protrusion may be configured with variable stiffness such that deformation in one direction requires less force than deformation in another direction.

As FIG. 2B makes apparent, the sizes of the protrusions 211 and 232 and the resulting diameters 215 and 237 are such that the protrusions 211 and 232 are expected to contact one another when they are generally at a shared longitudinal location. When the protrusions 211 and 232 are at a shared longitudinal position, the protrusions 211 and 232 exert mutual forces against one another. The protrusions 211 and 232 exert a contact force on one another as they pass one another during advancement of the catheter 102 over the guidewire 101. One or more of the following may be made of a deformable, elastic material which can flex in response to the forces the protrusions 211 and 232 exert on one another: guidewire 101, protrusions 211 (but not necessarily a remainder of the guidewire 101), catheter 102, and protrusion 232 (but not necessarily a remainder of the catheter 102). According to at least one exemplary embodiment, the guidewire 101 and protrusion 211 of the guidewire are nondeformable, but the catheter 102 and/or the catheter protrusion 232 are deformable. As a result, as the protrusion 232 of the catheter 102 makes contact with and presses against the protrusion 211 of the guidewire 101, one or more of diameter 237 and diameter 236 reversibly enlarge. Specifically, the diameter 237 may enlarge to a size at least equal to or larger than diameter 215.

Figure 2C:
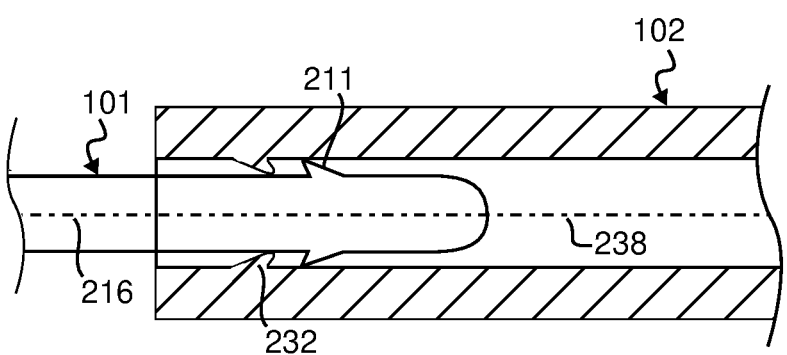
FIG. 2C shows a further stage of advancement of the catheter by which point the protrusion of the catheter has passed the protrusion of the guidewire.

FIG. 2C shows the guidewire 101 and the catheter 102 of FIG. 2A after the distal end of the catheter 102 has been advanced over the proximal end of the guidewire 101 to such a longitudinal extent that the respective protrusions have passed one another in the longitudinal/axial direction. As illustrated, protrusion 232 of the catheter 102 has advanced a small distance past the protrusion 211 of the guidewire 101.

FIGS. 2B and 2C show longitudinal axis 216 of guidewire 101 and a longitudinal axis 238 of catheter 102. Given the respective symmetries of the guidewire 101 and catheter 102, the longitudinal axes may also be referred to as center axes. During a state of use together, such as illustrated in FIGS. 2B and 2C, the guidewire 101 and catheter 102 are coaxial. That is to say the guidewire 101 and catheter 102 have a common longitudinal center axis 216/238. The first and second directions referred to above lie along the longitudinal center axis 216/238. Longitudinal location refers to one or more locations along the common axis 216/238. It should be appreciated that though the axis 216/238 is a straight line as depicted in the figures, the longitudinal axis may over some length, e.g. at least a centimeter or more, follow or at least be susceptible to following a meandering path. This is the natural result of both the guidewire 101 and catheter 102 being pliable over their lengths (despite having local material stiffness, especially in the case of the guidewire, an exemplary material for which is a metal or metal alloy).

Exemplary materials for a guidewire, including any protrusions thereof, include nitinol, which is an alloy of nickel and titanium. Exemplary materials for a catheter, including any protrusions thereof, include silicone rubber, nylon, polyurethane, polyethylene terephthalate (PET), latex, thermoplastic elastomers, and other polymers. Generally, materials now known and employed for guidewires and materials now known and employed for catheters may be suitably employed in embodiments according to this disclosure. Materials as yet not developed or not as yet applied to this medical application may also be appropriately employed without deviating from present embodiments.

Figure 2D:
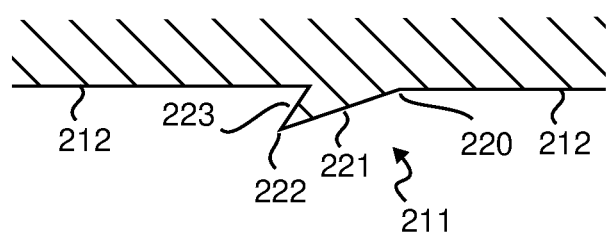
FIG. 2D shows an enlarged cross-sectional view of a protrusion of a guidewire.

FIG. 2D shows an enlarged cross-sectional plane of protrusion 211 of a guidewire. The protrusion 211 includes a front/lead surface 221 which is configured as a ramp or incline. The surface 221 is configured to gradually increase the cross-sectional diameter of guidewire 101 from point 220 to point 222. The surface 221 does not suddenly increase the cross-sectional diameter of the guidewire in this direction (though it may in the opposite direction). The surface 221 has an endpoint 222. The endpoint may have a radius of curvature that is more rounded than depicted in the figure. In a radial direction of the guidewire, a space or gap exists between the endpoint 222 and the external surface 212 of the main body 213 of the guidewire. The protrusion 211 forms a ledge such that a surface 223 (a back surface of the protrusion 211) is an underside of the ledge. In some embodiments the protrusion 211 may be configured to deflect into the space between the ledge and the external surface 212. In an alternative embodiment (not shown), the protrusion 211 may not form a ledge, and the surface 223 may be a backside but not an underside of the protrusion. In such case the protrusion 211 may have a longitudinal cross-sectional shape of a right triangle, for example.

Figure 2E:
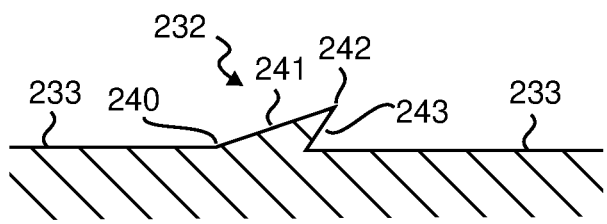
FIG. 2E shows an enlarged cross-sectional view of a protrusion of a catheter.

FIG. 2E shows an enlarged cross-sectional plane of protrusion 232 of a catheter. The protrusion 232 includes a front/lead surface 241 which is configured as a ramp or incline. The surface 241 is configured to gradually reduce the cross-sectional diameter of the lumen 231 of the catheter 102 from point 240 to point 242. The surface 241 does not suddenly decrease the cross-sectional diameter of the lumen in this direction (though it in may in the opposite direction). The surface 241 has an endpoint 242. The endpoint may have a radius of curvature that is more rounded than depicted in the figure. In a radial direction of the catheter, a space or gap exists between the endpoint 242 and the internal surface 233 of the catheter 102. The protrusion 232 forms a ledge with a surface 243 (a back surface of protrusion 232) forming an underside of the ledge. In some embodiments the protrusion 232 may be configured to deflect into the space between the ledge and the internal surface 233. In an alternative embodiment (not shown), the protrusion 242 may not form a ledge, and the surface 243 may be a backside but not an underside of the protrusion. In such case the protrusion 232 may have a longitudinal cross-sectional shape of a right triangle, for example.

Figure 3A:
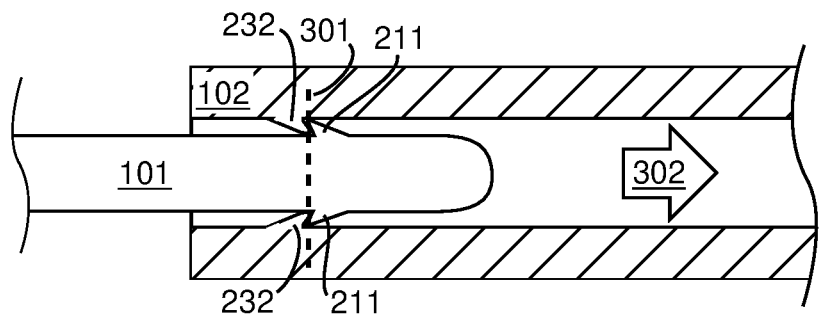
FIG. 3A illustrates the limit at which the back parts of the protrusions engage and prevent the guidewire from completely exiting the distal end of the catheter.

The shape, size, and material properties of the protrusions 211 and 232 are configured such that after the protrusions have been fully moved past one another during movement of the catheter 102 over the guidewire 101, the protrusions 211 and 232 are unable to (or at least substantially limited from) moving past one another in the opposite direction. FIG. 3A marks a boundary 301 with respect to the catheter 102 past which the guidewire 101 cannot move owing to the interaction of the protrusions 232 of the catheter and the protrusions 211 of the guidewire. In FIG. 3A, the respective protrusions have the ledge configurations discussed above in connection with FIGS. 2D and 2E. If the backsides of the protrusions 232 and 211 encounter one another physically at the longitudinal location of boundary 301, the undersides of their respective ledges come into contact and the protrusions physically hook one another and prevent further movement of either protrusion past the other. This locking behavior contrasts sharply with the general ease with which the protrusions may pass when encountering one another via their gradual ramped front surfaces. Arrow 302 shows the only direction with respect to boundary 301 which the guidewire 101 is permitted to move after the protrusions of guidewire and catheter lock.

Figure 3B:
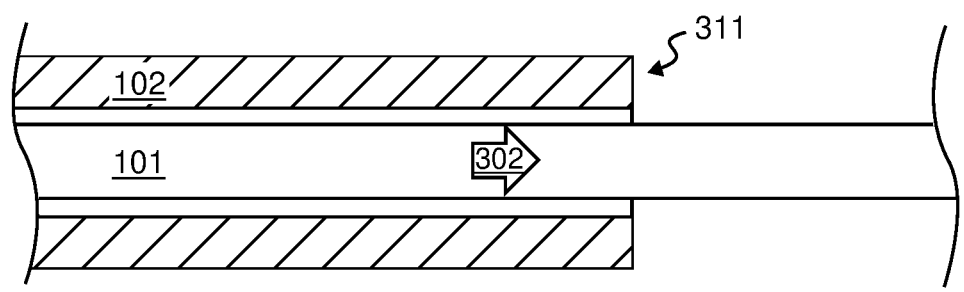
FIG. 3B illustrates the free exiting of the guidewire from a proximal end of the catheter.

It should be appreciated that the protrusions of the catheter and guidewire do not prevent or inhibit removal of the guidewire 101 from the catheter 102 when a medical practitioner has already placed the catheter 102 at a predetermined distance into a patient vessel or organ and now desires to remove the guidewire 101 altogether from the surgical site. FIG. 3B shows a proximal end 311 of catheter 102 with a proximal opening through which guidewire 101 is able to freely move in direction 302. In this way an entirety of the guidewire may be removed from the catheter while the catheter remains in place in the patient.

Figure 4A:
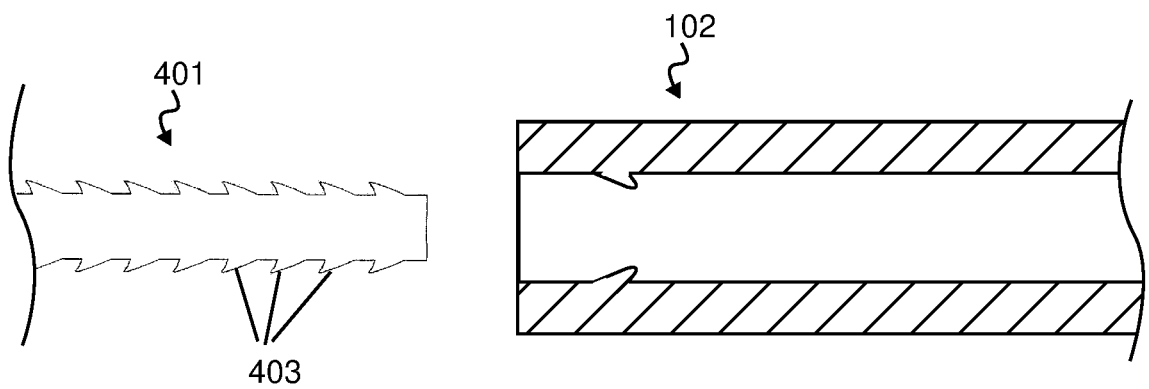
FIG. 4A shows an alternative guidewire which has a plurality of protrusion in series along the longitudinal axis.
Figure 4B:
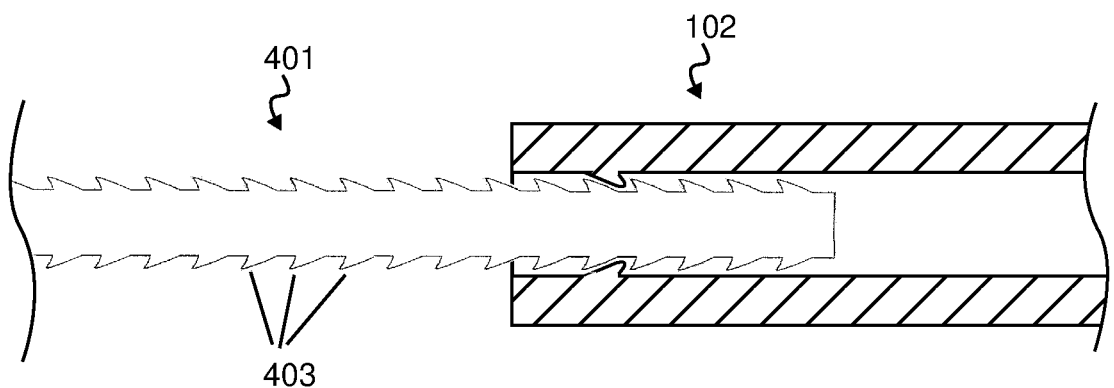
FIG. 4B illustrates advancement of a catheter with a protrusion advancing over the guidewire with multiple protrusions.

FIGS. 4A and 4B show an alternative embodiment with a different guidewire 401. The guidewire 401 may be used with catheter 102 or other catheters. The guidewire 401 comprises multiple protrusions 403 on an external surface of the guidewire. The protrusions 403 are spaced apart from one another at different longitudinal locations along the axis of the guidewire 401. The number of protrusions may be one, two, three, tens, dozens, or hundreds. For example, a single guidewire may have between 2 and 10 protrusions. A single guidewire may have between 5 and 20 protrusions. A single guidewire may have between 10 and 100 protrusions. The number of protrusions may be determined at the time of manufacture based on specifications, in particular the ease desired with which the guidewire may at least partially exit the distal end of the catheter after having already been inserted partially into the distal end of the catheter.

In the case of multiple protrusions, the longitudinal distance between adjacent or successive protrusions may vary from one embodiment to the next. The distance between any two adjacent protrusions in a longitudinal direction controls the maximum extent to which the guidewire may exit the distal end of the catheter (i.e., the maximum extent to which the distal end of the catheter may be withdrawn from overtop the guidewire by moving the catheter in the proximal direction) after the catheter has already been at least partially advanced over the guidewire (at least far enough such that the first protrusion of the catheter has passed the first protrusion of the guidewire). Exemplary distances between successive protrusion are 0.5 to 5.0 cm. In some embodiments (not shown) the catheter may have multiple protrusions spaced apart at different longitudinal locations.

Figure 5A:
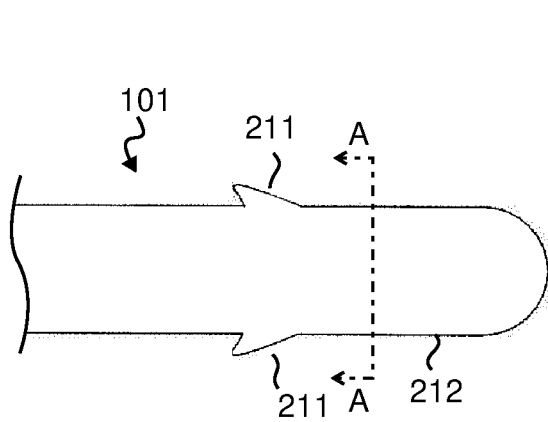
FIG. 5A indicates the position where a cross-sectional view A-A is taken from an exemplary guidewire.
Figure 5D:
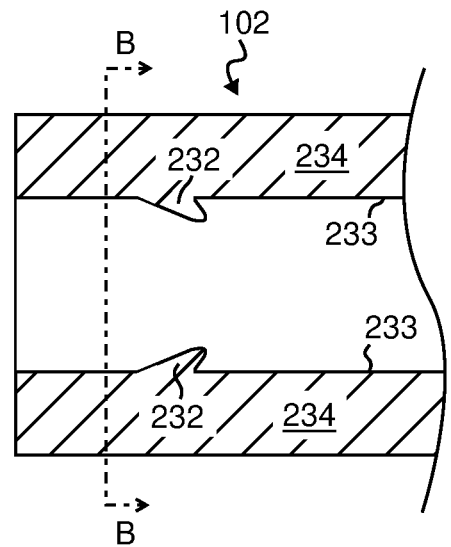
FIG. 5D indicates the position where a cross-sectional view B-B is taken from an exemplary catheter.
Figure 5B:
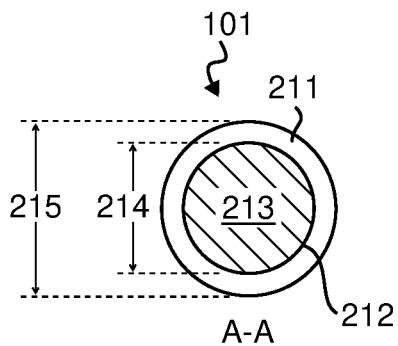
FIG. 5B shows the cross-sectional view A-A according to a first guidewire embodiment.
Figure 5E:
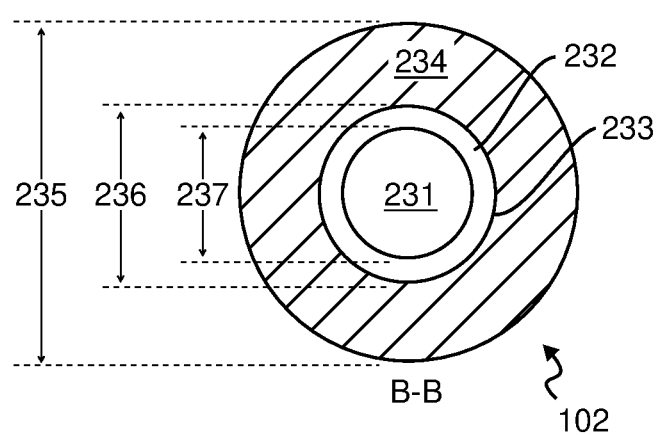
FIG. 5E shows the cross-sectional view B-B according to a first catheter embodiment.
Figure 5C:
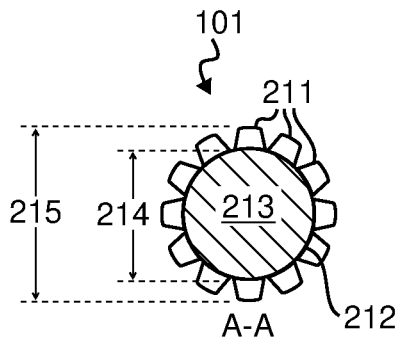
FIG. 5C shows the cross-sectional view A-A according to a second guidewire embodiment.

FIG. 5A shows again guidewire 101. A cross-section is taken at line A-A. A resulting cross-sectional view A-A is shown in FIG. 5B. An alternative configuration of guidewire 101 is shown in the cross-sectional view A-A of FIG. 5C. In FIG. 5B, the protrusion 211 is annular. The protrusion exists around a full circumference of the outer surface 212 of main body 213 of guidewire 101. In FIG. 5C, by contrast, the protrusion 211 comprises a plurality of (sub)protrusions each of which exists over only a segment of a circumference of surface 212. The term "subprotrusion" is used for convenience herein to refer to a plurality of protrusions at the same or substantially the same longitudinal location. The number of subprotrusions which collectively constitute a protrusion 211 may vary among embodiments. As illustrated in FIG. 5C the guidewire has twelve subprotrusions. If fewer than twelve subprotrusions are employed, the segment length about which the subprotrusion is arranged may be correspondingly larger. Subprotrusions may be the same size and shape, as in FIG. 5C, or else subprotrusions may vary from one another in size and/or shape. In any case, however, the largest cross-sectional diameter 215 of the guidewire at the location of protrusion 211 preferably does not exceed the diameter of the lumen of the catheter with which the guidewire is configured to be used.

Figure 5F:
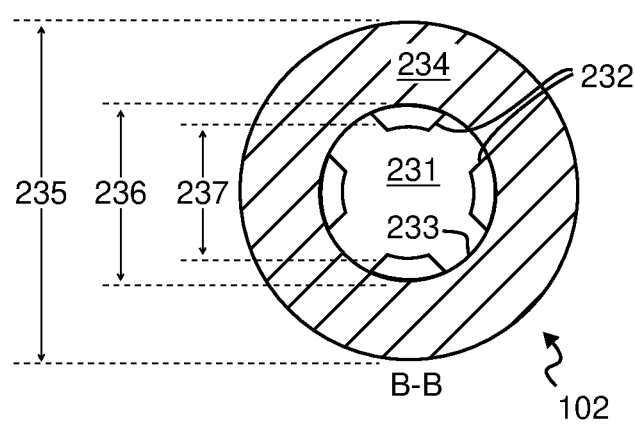
FIG. 5F shows the cross-sectional view B-B according to a second catheter embodiment.

FIG. 5D shows again catheter 102. A cross-section is taken at line B-B. A resulting cross-sectional view B-B is shown in FIG. 5E. An alternative configuration of catheter 102 is shown in the cross-sectional view B-B of FIG. 5F. In FIG. 5E, the protrusion 232 is annular. The protrusion exists about a full circumference of the inner surface 233 of the annular wall 234. In FIG. 5F, by contrast, the protrusion 232 comprises a plurality of (sub)protrusions each of which exists over only a segment of a circumference of surface 233. The term "subprotrusion" is used for convenience herein to refer to a plurality of protrusions at the same or substantially the same longitudinal location. The number of subprotrusions which collectively constitute a protrusion 232 may vary among embodiments. As illustrated in FIG. 5F the catheter has four subprotrusions. Subprotrusions may be the same size and shape, as in FIG. 5F, or else subprotrusions may vary from one another in size and/or shape. In any case, the diameters 235, 236, and 237 are as described above in connection with FIG. 2A, except that diameter 237 refers to a minimum diameter that exists at a protrusion 232.

In summary of FIGS. 4A, 4B, and 5A-5F, one or both the guidewire 101 and catheter 102 may have one protrusion or a plurality of protrusions. A plurality of protrusions may be at different longitudinal locations, at the same longitudinal location but different circumferential positions, or some combination of these. In embodiments with multiple protrusions at the same longitudinal location, gap sizes between adjacent protrusions are sized and positioned collectively so as to maintain the functional requirements that (i) the catheter protrusions are moveable past the guidewire protrusions in a first direction and (ii) the catheter protrusions are immovable past the guidewire protrusions in a second direction, wherein the first and second directions are opposite one another.

Figure 6A:
FIGS. 6A, 6B, and 6C show a multicomponent guidewire.
Figure 6B:
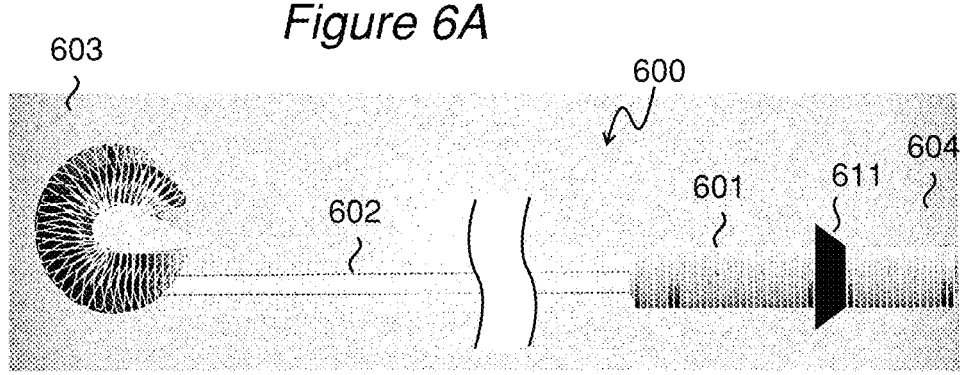
Figure 6C:
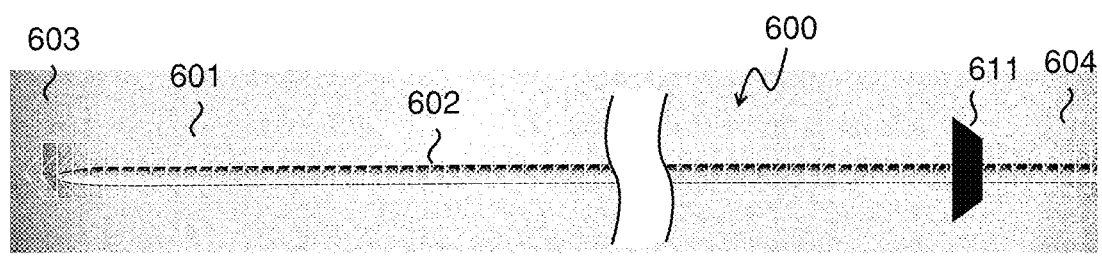

FIGS. 6A, 6B, and 6C show various depictions of a guidewire 600, including both a distal end 603 and a proximal end 604. Guidewire 600 includes both an outer part 601 and inner part 602. Generally the inner part 602 may not be visible, as in FIG. 6A. In FIG. 6B part of the outer part 601 is depicted as translucent to permit viewing of the inner part 602. In FIG. 6C an entirety of the outer part 601 is depicted as translucent to permit viewing of the inner part 602. Both the inner and outer parts 601 and 602 are flexible. The inner part 602 is moveable with respect to the outer part 601 to change a configuration of the distal end of the guidewire 600, as illustrated by the contrast of FIG. 6B and FIG. 6C. A protrusion 611 in accordance with this disclosure is arranged at the proximal end 604 on or integrally formed with outer part 601.

FIGS. 7A-7L and 8A-8J illustrate a series of steps to a method of catheterization. The figures are organized into columns on each sheet. Figures which share a row (e.g., FIG. 7A and FIG. 8A) illustrate the same step but, in the left column, from an external view, and in the right column, from a view inside the vessel being catheterized. With a few exceptions, each row is a single step. In a few instances, a few rows are used to illustrate a single step. These will be identified in the following description.

Figure 7A:
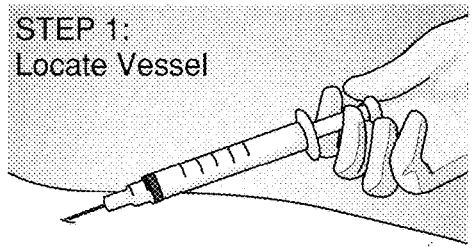
FIGS. 7A-7L show steps of an exemplary method of catheterization from a view external to a patient.
Figure 8A:
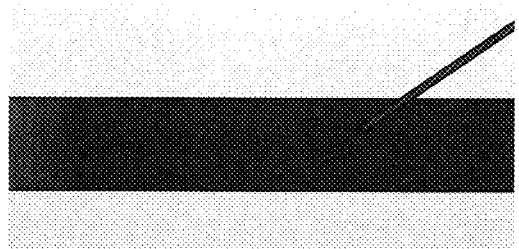
FIGS. 8A-8J show the same exemplary method from an internal view.
Figure 7B:
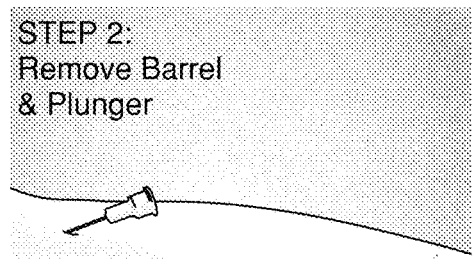
Figure 8B:
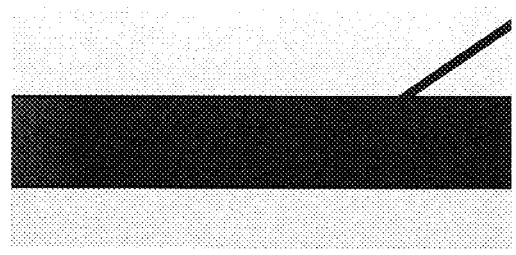
Figure 7C:
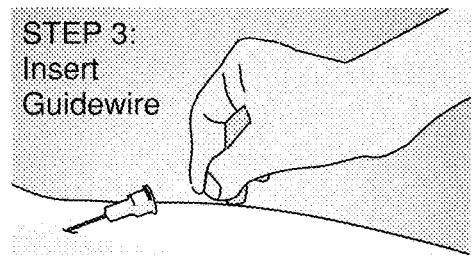
Figure 8C:
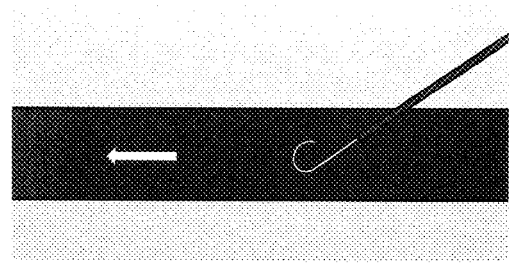
Figure 7D:
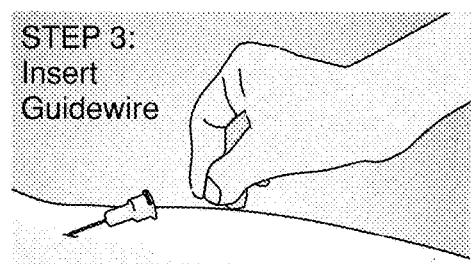
Figure 8D:
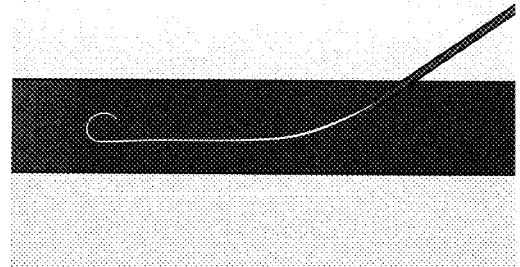

FIGS. 7A and 8A show a step of locating a blood vessel with the needle of a syringe. Ultrasound may be used to visually track the location of the needle. After the vessel is located, the barrel and plunger are removed while the needle remains in place inserted in the blood vessel, as shown in FIGS. 7B and 8B. In FIGS. 7C and 8C a distal end of a guidewire is inserted into the blood vessel via a lumen of the needle. FIGS. 7D and 8D show continuation of the guidewire insertion step. The guidewire is inserted a predetermined distance into the vessel, for example 10 to 40 mm. Ultrasound or another imaging technique may be used during the guidewire insertion step to visually track the advancement of the guidewire.

Figure 7E:
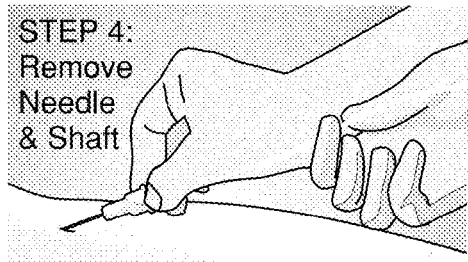
Figure 8E:
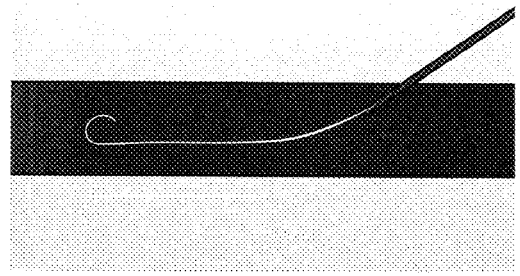
Figure 7F:
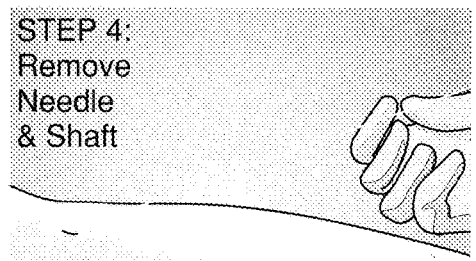
Figure 8F:
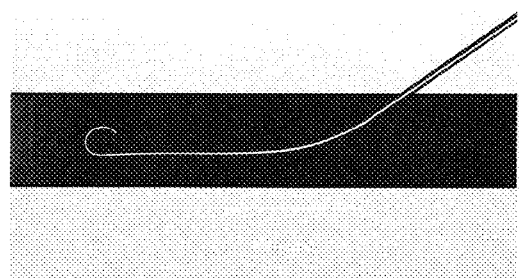

FIGS. 7E and 8E show the start of the next step, namely removing the needle from the blood vessel while leaving the distal end of the guidewire in the blood vessel. Generally best efforts are made at this step to keep the guidewire substantially in the same position and location relative to the patient while the needle is slid over and off the proximal end of the guidewire. FIGS. 7F and 8F show the end of the needle removal step at which point the guidewire remains in place in the vessel but the needle is gone.

Figure 7G:
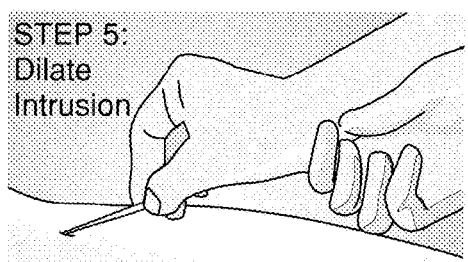
Figure 8G:
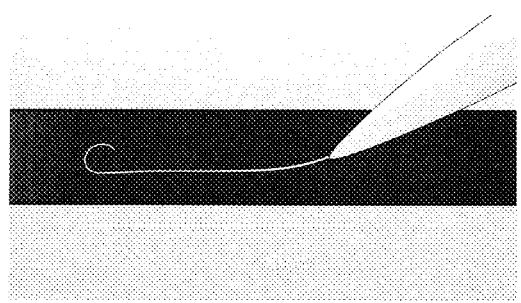
Figure 7H:
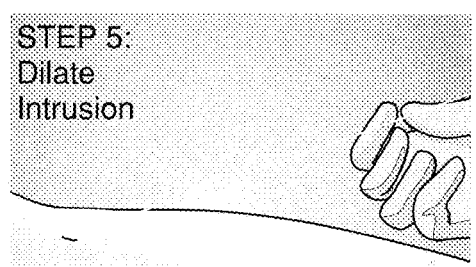
Figure 8H:
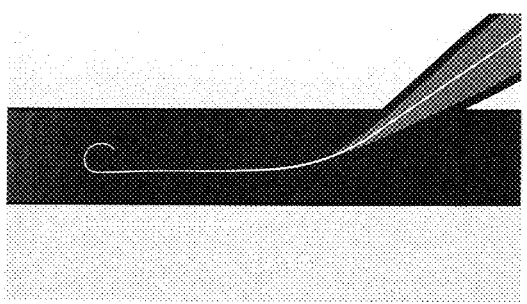

FIGS. 7G and 8G show the next step of dilating the intrusion in the patient's skin presently maintained by the guidewire. The dilator is slid over the proximal end of the guidewire and down the guidewire until it meets the patient's skin. The medical practitioner then gently pushes in and moves the dilator to expand the intrusion. FIGS. 7H and 8H show the end of the dilation step at which point the dilator is removed, leaving a larger incursion into the patient's body then before dilation. Through the process of the dilation best efforts are made to keep the distal end of the guidewire substantially in the same position and location within the vessel. This can be difficult at times since the dilator must be strung along an entirely of the portion of guidewire which is outside the patient.

Figure 7I:
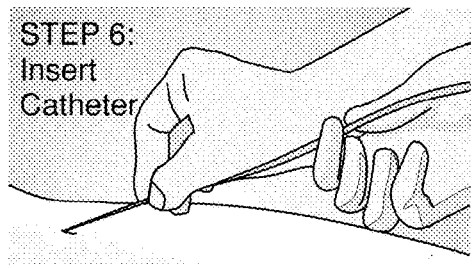
Figure 8I:
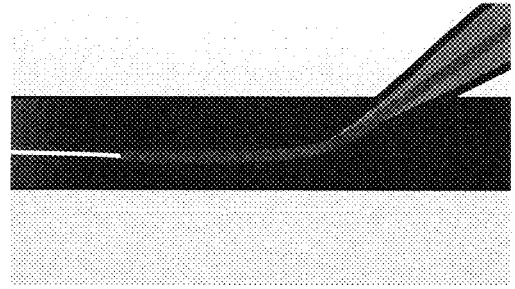
Figure 7J:
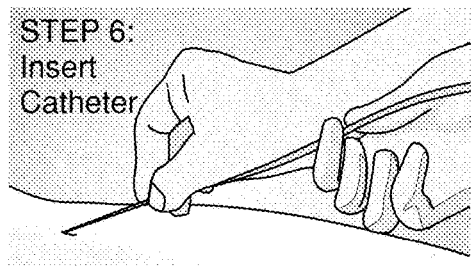
Figure 8J:
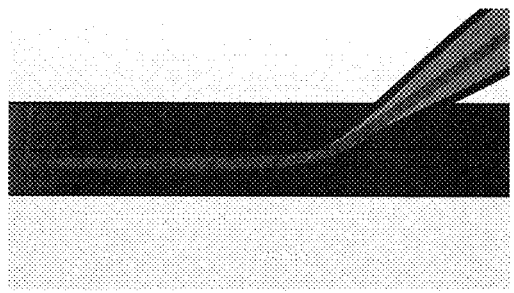

FIGS. 7I and 8I show the next step of inserting the catheter. FIGS. 7J and 8J show the continuation of this step as the catheter is advanced further into the patient and into the patient's vessel. It is at this step of catheter insertion that the catheter is strung over the guidewire and the respective protrusions of the guidewire and catheter pass one another as discussed above and illustrated in prior figures. After the catheter has been advanced over the guidewire the predetermined distance required for the protrusions to meet and pass one another along the longitudinal center axis, complete withdrawal of the catheter will also result in withdrawal of the guidewire owing to engaging of the backsides of the respective protrusions.

Stated more generally, at the catheter insertion steps illustrated by FIGS. 7I, 8I, 7J, and 8J, the protrusions of the guidewire and catheter are configured to cooperate with one another such that (i) the catheter protrusion is moveable past the guidewire protrusion in a first direction and (ii) the catheter protrusion is immovable past the guidewire protrusion in a second direction, wherein the first and second directions are opposite one another. The first direction entails the catheter being moved toward and into the patient. The second direction entails the catheter being moved out of and away from the patient.

Figure 7K:
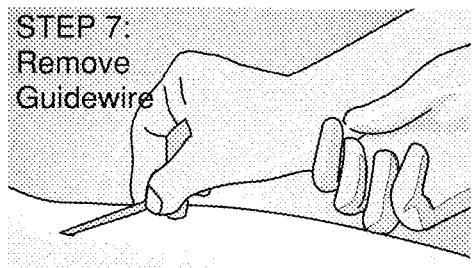
Figure 7L:
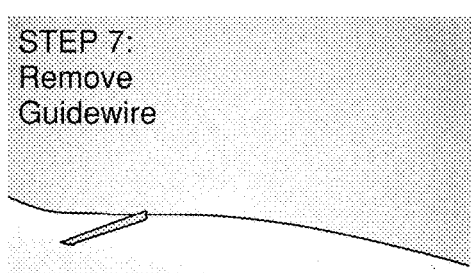

After the catheter is inserted the desired predetermined distance into the blood vessel, the guidewire is no longer needed and is removed as illustrated by FIG. 7K. The protrusions of the guidewire and catheter do not interfere or inhibit the movement of the guidewire out from the proximal end of the catheter, as was discussed above in connection with FIG. 3B. At last only the catheter remains, as shown in FIG. 7L.

Figures 9A, 9B:
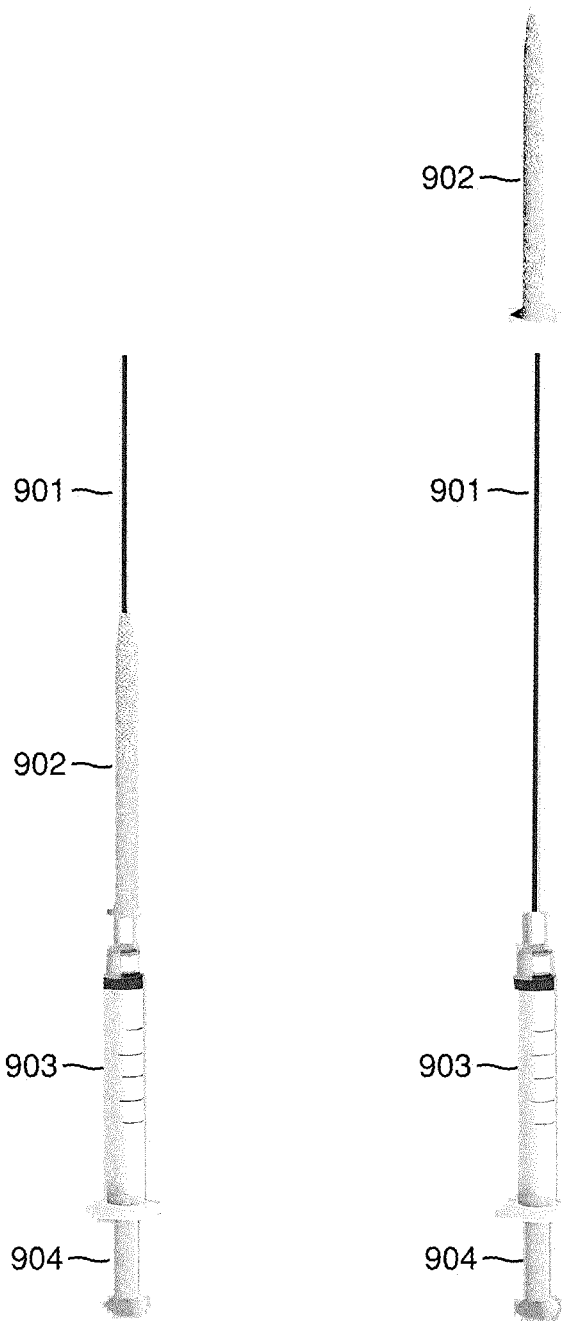
FIGS. 9A and 9B show an embodiment with an alternative syringe and dilator configuration.

FIGS. 9A and 9B show elements of a further embodiment which reduces the number of steps in the catherization procedure just described. This further embodiment is usable with conventional guidewires and catheters as well as with new guidewires and catheters according to this disclosure. As shown by FIGS. 9A and 9B, the needle 901 and dilator 902 are configured (e.g., in size such as length) so that the dilator 902 may be slid over the needle 901 while leaving a distal end of the needle still exposed and usable for finding a blood vessel. FIG. 9A shows the dilator 902 positioned on the needle 901. FIG. 9B shows the dilator 902 slid off the needle 901. The needle 901 is removably connected with a barrel 903 and plunger 904. Both the barrel 903 and plunger 904 may be identical to barrels and plungers conventionally used prior to the present invention.

FIGS. 10A-10J and 11A-11H illustrate a series of steps to another method of catheterization. As before, the figures are organized into columns on each sheet. Figures which share a row (e.g., FIGS. 10A and 11A) illustrate the same step but, in the left column, from an external view, and in the right column, from a view inside the vessel being catheterized. Generally a row corresponds with a single step. In a few instances, a few rows are used to illustrate a single step. These will be identified in the following description.

Figure 10A:
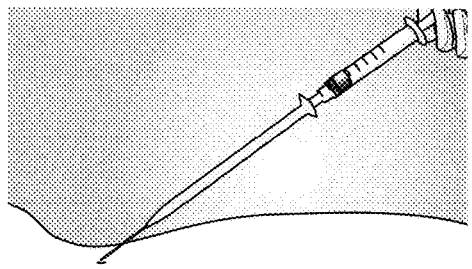
FIGS. 10A-10J show steps of another exemplary method of catheterization from a view external to a patient.
Figure 10B:
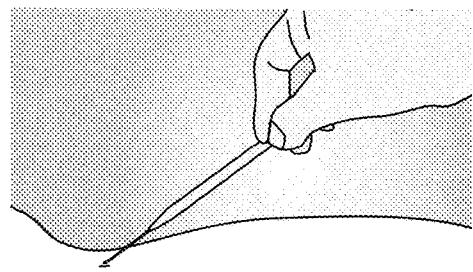
Figure 10C:
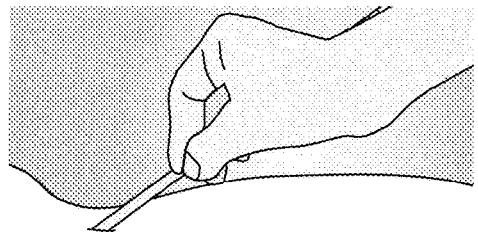
Figure 11A:
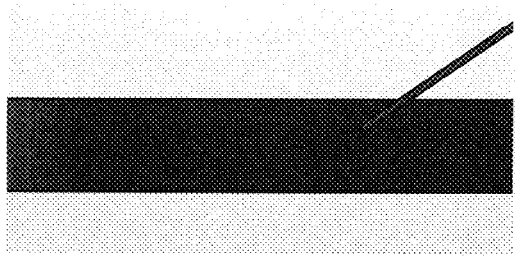
FIGS. 11A-11H show the same exemplary method from an internal view.
Figure 11B:
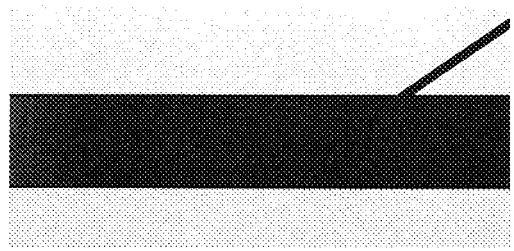
Figure 11C:
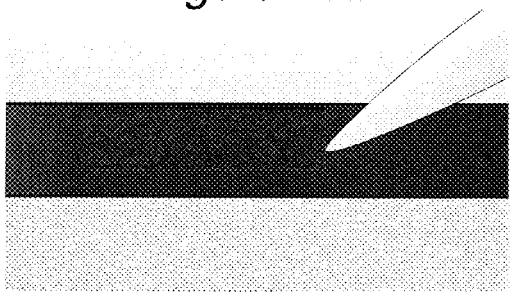

FIGS. 10A and 11A show a step of locating a blood vessel with the needle of a syringe, specifically a distal part of the needle. This step may be assisted with ultrasound imaging. At this step the dilator is on a proximal part of the needle. FIGS. 10B/11B and 10C/11C show the next step, namely dilating the intrusion in the patient's skin presently maintained by the needle. The dilator is slid down from the proximal end of the needle to the distal end and into the intrusion. The medical practitioner then gently pushes in and moves the dilator to expand the intrusion.

Figure 10D:
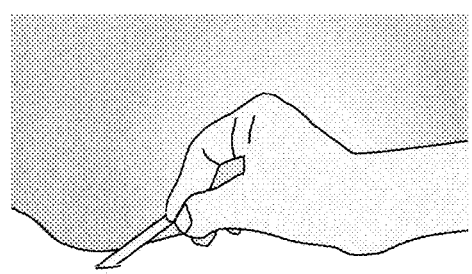
Figure 11D:
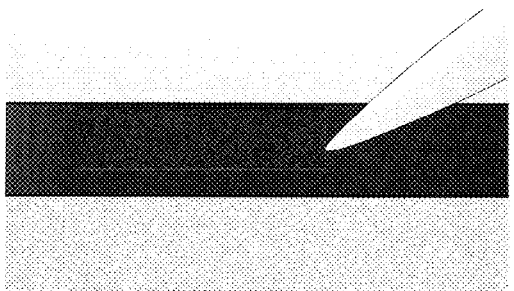

At the end of the dilation step, the entire syringe, including needle, barrel, and plunger, are removed while the dilator remains in place keeping open the intrusion. This is shown in FIGS. 10D and 11D.

Figure 10E:
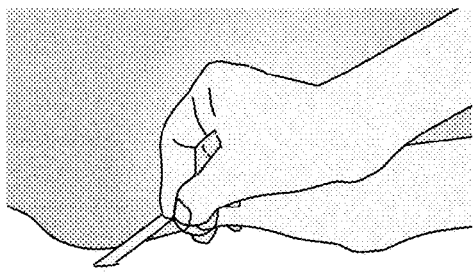
Figure 11E:
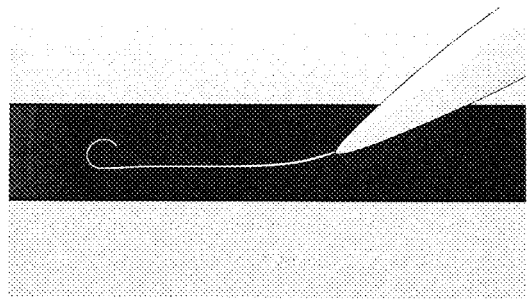
Figure 10F:
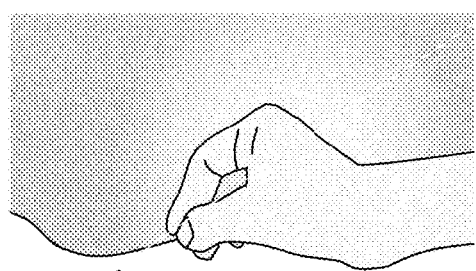
Figure 11F:
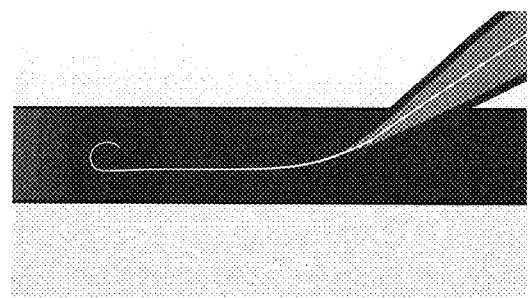

In FIGS. 10E and 11E a distal end of a guidewire is inserted into the blood vessel via a lumen of the dilator. After the guidewire has been advanced a desired predetermined distance (for example 10 to 40 mm) in the vessel, the dilator is removed, as shown in FIGS. 10F and 11F. Ultrasound or another imaging technique may be used during the guidewire insertion step to visually track the advancement of the guidewire.

Figure 10G:
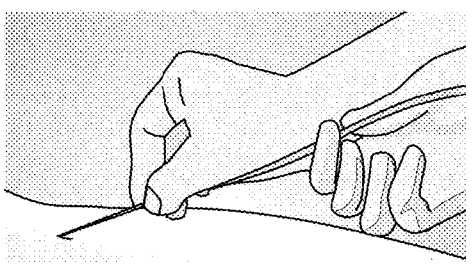
Figure 11G:
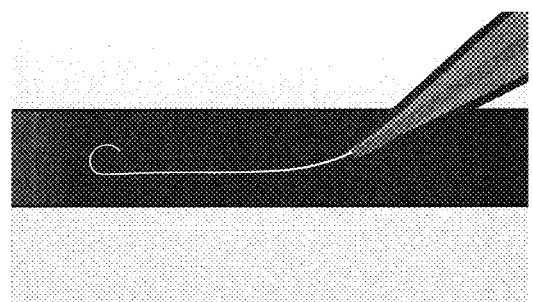
Figure 10H:
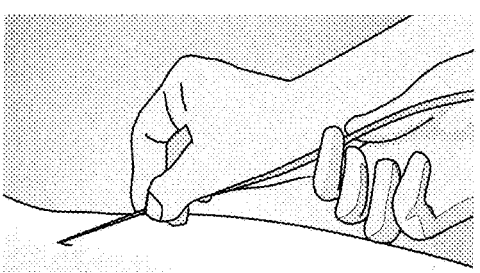
Figure 11H:
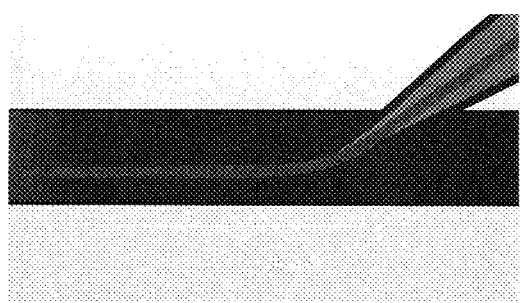

FIGS. 10G and 11G show the next step of inserting the catheter. FIGS. 10H and 11H show the continuation of this step as the catheter is advanced further into the patient and into the patient's vessel. It is at this step of catheter insertion that the catheter is strung over the guidewire and the respective protrusions of the guidewire and catheter pass one another as discussed above, if indeed new guidewires and catheters are used in the procedure. As stated before, the method illustrated by FIGS. 10A-10J and 11A-11H may be employed with new or conventional guidewires and also new or conventional catheters.

Figure 10I:
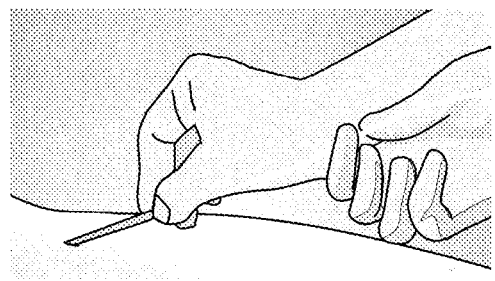
Figure 10J:
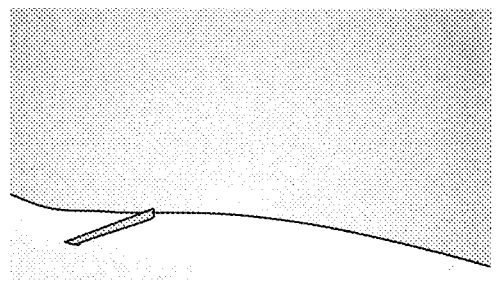

After the catheter is inserted the desired predetermined distance into the blood vessel, the guidewire is no longer needed and is removed as illustrated by FIG. 10I. The protrusions of the guidewire and catheter, if present, do not interfere or inhibit the movement of the guidewire out from the proximal end of the catheter, as was discussed above in connection with FIG. 3B. At last only the catheter remains, as shown in FIG. 10J.

Exemplary guidewires, catheters, and methods according to the invention may be used in a variety of vascular access scenarios. Exemplary guidewires may be used for applications in emergency medicine, critical care, surgery, interventional radiology, vascular surgery, cardiology, and pediatrics. Exemplary guidewires may be used for stent placement, feeding tube placement, and drainage tube placement in many medical specialties.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be separated from or combined with the features of any of the other several embodiments without departing from the scope or spirit of the present invention.

While exemplary embodiments of the present invention have been disclosed herein, one skilled in the art will recognize that various changes and modifications may be made without departing from the scope of the invention as defined by the following claims.

What is claimed is:

1. A system for reducing or preventing unintentional advancement of a guidewire during catheterization, comprising
    a guidewire with a plurality of guidewire protrusions on an external surface of the guidewire, wherein a main body of the guidewire has a first diameter which is the main body's largest diameter, wherein the guidewire has a second diameter at the longitudinal position of the at least one guidewire protrusion, wherein the second diameter is greater than the first diameter, and wherein the guidewire has the first diameter on both sides of at least one of the plurality of protrusions; and
    a catheter with a lumen and at least one catheter protrusion on an internal surface of the catheter,
    wherein the first diameter of the guidewire is smaller than all diameters of the lumen of the catheter,
    wherein the plurality of guidewire protrusions of the guidewire and the at least one catheter protrusion of the catheter are configured to cooperate with one another such that (i) the catheter protrusion is moveable past a guidewire protrusion of the plurality of guidewire protrusions in a first direction and (ii) the at least one catheter protrusion is immoveable past the guidewire protrusion in a second direction, wherein the first and second directions are opposite one another,
    wherein the guidewire has the plurality of guidewire protrusions arranged at different longitudinal locations.

2. The system of claim 1,
    wherein the guidewire has a first cross-sectional size at a guidewire protrusion of the plurality of guidewire protrusions,
    wherein the lumen has a second cross-sectional size at the at least one catheter protrusion, and
    wherein the first cross-sectional size is greater than the second cross-sectional size.

3. The system of claim 1, wherein:
    at least one guidewire protrusion of the plurality of guidewire protrusions is nondeformable; and
    a body of the catheter and/or the at least one catheter protrusion is deformable.

4. The system of claim 1, wherein the at least one catheter protrusion is configured with variable stiffness such that deformation in one direction requires less force than deformation in another direction.

5. The system of claim 1, wherein a guidewire protrusion of the plurality of guidewire protrusions is at a proximal end of the guide wire and wherein the at least one catheter protrusion is at a distal end of the catheter.

6. The system of claim 1, wherein the guidewire and catheter are coaxial such that they have a common longitudinal center axis, the first and second directions lie along the longitudinal center axis, the first direction is along the center axis toward a distal end of the guidewire, and the second direction is along the center axis toward a proximal end of the guidewire.

7. The system of claim 1, wherein the catheter has a plurality of protrusions.

8. The system of claim 7, wherein at least some of the plurality of protrusions are arranged at a single longitudinal location.

9. The system of claim 1, wherein:
    at least one guidewire protrusion of the plurality of guidewire protrusions is nearer a proximal end of the guidewire than a distal end of the guidewire in a state of use during catheterization; and
    the at least one catheter protrusion is nearer a distal end of the catheter than a proximal end of the catheter in a state of use during catheterization.

* * * * *